United States Patent
Wu

[11] Patent Number: 6,159,945
[45] Date of Patent: Dec. 12, 2000

[54] 9-AMINO-3-KETO ERYTHROMYCIN DERIVATIVES

[75] Inventor: Yong-Jin Wu, East Lyme, Conn.

[73] Assignee: Pfizer Inc., New York, N.Y.

[21] Appl. No.: 09/402,338

[22] PCT Filed: Oct. 9, 1998

[86] PCT No.: PCT/IB98/01578

§ 371 Date: Oct. 6, 1999

§ 102(e) Date: Oct. 6, 1999

[87] PCT Pub. No.: WO99/21866

PCT Pub. Date: May 6, 1999

Related U.S. Application Data

[60] Provisional application No. 60/063,676, Oct. 29, 1997.

[51] Int. Cl.$^7$ ............................. A61K 31/70; C07H 17/08
[52] U.S. Cl. ............................. 514/29; 536/7.2; 536/7.4; 536/18.5
[58] Field of Search ............................. 536/7.2, 7.9, 18.5; 579/29

[56] References Cited

FOREIGN PATENT DOCUMENTS

WO 98/51695  11/1998  WIPO .

Primary Examiner—Elli Peselev
Attorney, Agent, or Firm—Peter C. Richardson; Paul H. Ginsburg; Jolene W. Appleman

[57] ABSTRACT

The invention relates to compounds of the formula I

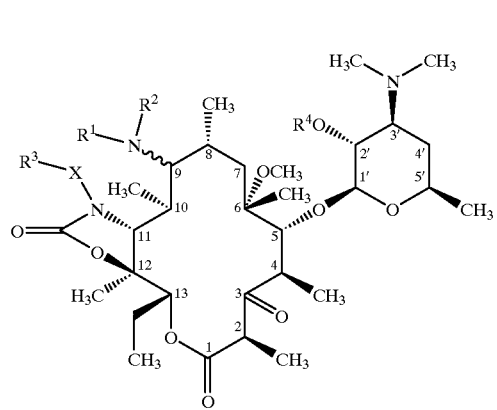

and to pharmaceutically acceptable salts thereof, wherein $R^1$, $R^2$, $R^3$, $R^4$ and X are as defined herein. The invention also relates to pharmaceutical compositions containing the compounds of formula I, methods of using said compounds of formula I in the treatment of infections, and methods of preparing said compounds of formula I.

14 Claims, No Drawings

9-AMINO-3-KETO ERYTHROMYCIN DERIVATIVES

This application claims benefit of provisional application Ser. No. 60/063,676 filed Oct. 29, 1997.

BACKGROUND OF THE INVENTION

This invention relates to novel 9-amino-3-keto-11,12-carbazate or carbamate derivatives of 6-O-methylerythromycin A. The compounds of this invention are useful as antibiotic agents in mammals, including man, as well as in fish and birds. The compounds of the present invention are broad-spectrum macrolide antibiotics that are effective against infections caused by certain gram-positive and gram-negative bacteria as well as protozoa. Various derivatives of erythromycin A useful as antibiotic agents are referred to in U.S. patent application Ser. No. 60/049,349, filed Jun. 11, 1997, and U.S. patent application Ser. No. 60/046,150, filed May 9, 1997, both of which are incorporated herein by reference in their entirety.

SUMMARY OF THE INVENTION

The present invention relates to compounds of the formula I

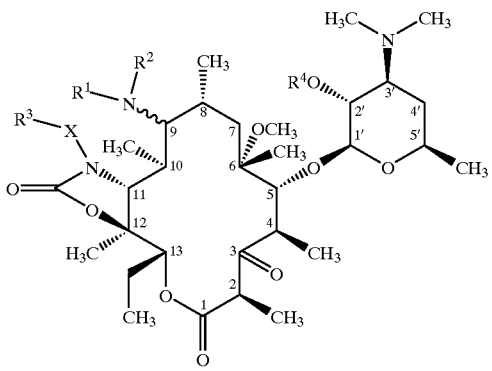

I or a pharmaceutically acceptable salt thereof, wherein:
X is $-CR^5R^6-$ or $-NR^5-$ or $-O-$;
or X is taken together with $R^3$ to form $-N=CR^7R^8$;
or X and $R^3$ are taken together to form a heterocyclic ring of the formula XI

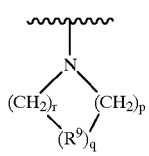

XI wherein in said ring of formula XI, r and p are each independently an integer ranging from 1 to 3, q is 0 or 1, and $R^9$ is $-CH_2-$, $-O-$, $-S-$, $-C(O)-$, $-C(S)-$, $-SO_2-$, $-CH=CH-$, $-CH(OH)CH(OH)-$, or $-NH-$; and wherein the $(CH_2)_r$ and $(CH_2)_p$ portions of said ring of formula XI are optionally substituted by 1 to 4 substituents, and the nitrogen atom where $R^9$ is $-NH-$ is optionally substituted by 1 substituent, and each hydrogen atom of $R^9$ where $R^9$ is $-CH_2-$, $-CH=CH-$, or $-CH(OH)CH(OH)$ is optionally substituted by one substituent, said optional substituents being independently selected from the group consisting of $-C(O)O(C_1-C_{10}$ alkyl), $C_1-C_{10}$ alkoxy, $C_1-C_{10}$ alkanoyl, halo, nitro, cyano, 4–10 membered heterocyclic, $C_1-C_{10}$ alkyl, $-NR^5R^6$, $C_6-C_{10}$ aryl, $-S(O)_n$ $(C_1-C_{10}$ alkyl) wherein n is an integer ranging from 0 to 2, and $-SO_2NR^5R^6$;

each $R^1$ and $R^2$ is independently selected from H and $C_1-C_{12}$ alkyl, wherein one or two carbons of said alkyl are optionally replaced by a heteroatom selected from O, S and N, and are optionally substituted by 1 to 3 substituents selected from the group consisting of $-C(O)O(C_1-C_{10})$ alkyl, $-O(C_1-C_{10})$alkyl, $C_1-C_{10}$ alkanoyl, halo, nitro, cyano, $C_1-C_{10}$ alkyl, 4–10 membered heterocyclic, $C_6-C_{10}$ aryl, $-N(C_1-C_{10})$alkyl, $-S(C_1-C_{10})$alkyl), $-SO(C_1-C_{10})$ alkyl, $-SO_2(C_1-C_{10})$alkyl and $-SO_2N(C_1-C_{10})$alkyl;

or $R^1$ and $R^2$ are taken together with the nitrogen atom to which they are linked to form $-N=CR^7R^8$;

or $R^1$ and $R^2$ are taken together with the nitrogen atom to which they are linked to form a heterocyclic ring of the formula XI

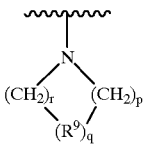

XI wherein in said ring of formula XI, r and p are each independently an integer ranging from 1 to 3, q is 0 or 1, and $R^9$ is $-CH_2-$, $-O-$, $-S-$, $-C(O)-$, $-C(S)-$, $-SO_2-$, $-CH=CH-$, $-CH(OH)CH(OH)-$, or $-NH-$; and wherein the $(CH_2)_r$ and $(CH_2)_p$ portions of said ring of formula XI are optionally substituted by 1 to 4 substituents, and the nitrogen atom where $R^9$ is $-NH-$ is optionally substituted by 1 substituent, and each hydrogen atom of $R^9$ where $R^9$ is $-CH_2-$, $-CH=CH-$, or $-CH(OH)CH(OH)$ is optionally substituted by one substituent, said optional substituents being independently selected from the group consisting of $-C(O)O(C_1-C_{10}$ alkyl), $C_1-C_{10}$ alkoxy, $C_1-C_{10}$ alkanoyl, halo, nitro, cyano, 4–10 membered heterocyclic, $C_1-C_{10}$ alkyl, $-NR^5R^6$, $C_6-C_{10}$ aryl, $-S(O)_n$ $(C_1-C_{10}$ alkyl) wherein n is an integer ranging from 0 to 2, and $-SO_2NR^5R^6$;

$R^3$ is H, $R^7$, $-C(O)R^7$, $C(O)R^{10}$, $-C(O)OR^7$, $-C(O)OR^{10}$, or $-(CR^5R^6)_mR^{10}$, wherein m is an integer ranging from 0 to 6 and both $R^5$ and $R^6$ may vary for each iteration where m is greater than 1;

$R^4$ is H, $-C(O)R^{10}$ or $C_1-C_{18}$ alkanoyl, wherein in the alkyl portion of said alkanoyl one or two carbons optionally may be replaced by a heteroatom selected from O, S and N;

each $R^5$ and $R^6$ is independently H or $C_1-C_6$ alkyl;

each $R^7$ and $R^8$ is independently selected from H and $C_1-C_{12}$ alkyl, wherein one or two carbons of said alkyl are optionally replaced by a heteroatom selected from O, S and N, and are optionally substituted by 1 to 3 substituents selected from the group consisting of $-C(O)O(C_1-C_{10})$alkyl, $-O(C_1-C_{10})$alkyl, $C_1-C_{10}$ alkanoyl, halo, nitro, cyano, $C_1-C_{10}$ alkyl, 4–10 membered heterocyclic, $C_6-C_{10}$ aryl, $-N(C_1-C_{10})$alkyl, $-S(C_1-C_{10}$ alkyl), $-SO(C_1-C_{10})$alkyl, $-SO_2(C_1-C_{10})$alkyl and $-SO_2N(C_1-C_{10})$alkyl; and $R^{10}$ is a 4–10 membered heterocyclic or $C_6-C_{10}$ aryl; wherein said heterocyclic and aryl groups are optionally substituted by 1 to 3 substituents independently selected from the group consisting of 4–10 membered heterocyclic, $C_6$–$C_{10}$ aryl, —NHC(O)($C_1$–$C_{10}$)alkyl, —NHC(O)N ($C_1$–$C_{10}$)alkyl, —C(O)O($C_1$–$C_{10}$)alkyl, —O($C_1$–$C_{10}$)alkyl, $C_1$–$C_{10}$ alkanoyl, halo, nitro, cyano, ($C_1$–$C_{10}$), alkyl, —N($C_1$–$C_{10}$)alkyl, —S($C_1$–$C_{10}$ alkyl), —SO($C_1$–$C_{10}$) alkyl), —SO$_2$($C_1$–$C_{10}$)alkyl and —SO$_2$N($C_1$–$C_{10}$)alkyl.

More specific embodiments of this invention include compounds of formula I wherein $R^4$ is H.

More specific embodiments of this invention include compounds of formula I wherein X is —NH—.

More specific embodiments of this invention include compounds of formula I wherein $R^1$ is H.

More specific embodiments of this invention include compounds of formula I wherein $R^1$ is H and $R^2$ is H, methyl, ethyl, isopropyl, propyl, or cyclopropyl.

Other more specific embodiments of this invention include compounds of formula I wherein $R^3$ is $(CH_2)_m R^{10}$ wherein m is an integer ranging from 0 to 6 and $R^{10}$ is as defined above.

More specific embodiments of this invention include compounds of formula I wherein $R^{10}$ is a 4–10 membered heterocyclic.

Specific embodiments of $R^{10}$ include quinolinyl, 4-phenyl-1-imidazol-1-yl, imidazo(4,5-b)pyridin-3-yl and 4-pyridin-3-yl-imidazol-1-yl.

Examples of preferred compounds of this invention include compounds of formula I selected from the group consisting of:

9-Deoxo-9-amino-11-deoxy-5-O-desosaminyl-11-(3-quinolin-4-yl-propyl)hydrazo-6-O-methyl-3-oxoerythronolide A, 11,12-carbamate;

9-Deoxo-9-methylamino-11-deoxy-5-O-desosaminyl-11-(3-quinolin-4-yl-propyl)hydrazo-6-O-methyl-3-oxoerythronolide A, 11,12-carbamate;

9-Deoxo-9-ethylamino-11-deoxy-5-O-desosaminyl-11-(3-quinolin-4-yl-propyl)hydrazo-6-O-methyl-3-oxoerythronolide A, 11,12-carbamate;

9-Deoxo-9-propylamino-11-deoxy-5-O-desosaminyl-11-(3-quinolin-4-yl-propyl)hydrazo-6-O-methyl-3-oxoerythronolide A, 11,12-carbamate;

9-Deoxo-9-isopropylamino-11-deoxy-5-O-desosaminyl-11-(3-quinolin-4-yl-propyl)hydrazo-6-O-methyl-3-oxoerythronolide A, 11,12-carbamate;

9-Deoxo-9-cyclopropylamino-11-deoxy-5-O-desosaminyl-11-(3-quinolin-4-yl-propyl)hydrazo-6-O-methyl-3-oxoerythronolide A, 11,12-carbamate;

9-Deoxo-9-amino-11-deoxy-5-O-desosaminyl-11-(3-(7-methoxy-quinolin-4-yl)-propyl))hydrazo-6-O-methyl-3-oxoerythronolide A, 11,12-carbamate;

9-Deoxo-9-amino-1-deoxy-5-O-desosaminyl-11-(3-benzoimidazol-1-yl-propyl)hydrazo-6-O-methyl-3-oxoerythronolide A, 11,12-carbamate;

9-Deoxo-9-amino-11-deoxy-5-O-desosaminyl-11-(3-indol-1-yl-propyl)hydrazo-6-O-methyl-3-oxoerythronolide A, 11,12-carbamate;

9-Deoxo-9-amino-11-deoxy-5-O-desosaminyl-11-(3-indazol-1-yl-propyl)hydrazo-6-O-methyl-3-oxoerythronolide A, 11,12-carbamate;

9-Deoxo-9-amino-11-deoxy-5-O-desosaminyl-11-(3-carbazol-1-yl-propyl)hydrazo-6-O-methyl-3-oxoerythronolide A, 11,12-carbamate;

9-Deoxo-9-amino-11-deoxy-5-O-desosaminyl-11-(3-(5-phenyl-1H-pyrrol-2-yl)-propyl)hydrazo-6-O-methyl-3-oxoerythronolide A, 11,12-carbamate;

9-Deoxo-9-amino-11-deoxy-5-O-desosaminyl-11-(3-(4-phenyl-imidazol-1-yl)-propyl)hydrazo-6-O-methyl-3-oxoerythronolide A, 11, 12-carbamate;

9-Deoxo-9-methylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-ethylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-propylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-isopropylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-cyclopropylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-amino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-methylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-ethylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-propylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-isopropylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-cyclopropylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-amino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-methylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-ethylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-propylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-isopropylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-cyclopropylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-amino-11-deoxy-5-O-desosaminyl-11-(3-(3-(4-chlorophenyl)-(1,2,4)oxadizol-5-yl)-propyl)hydrazo-6-O-methyl-3-oxoerythronolide A, 11,12-carbamate;

9-Deoxo-9-amino-11-deoxy-5-O-desosaminyl-11-(3-(3-(4-methoxyphenyl)-(1,2,4)oxadizol-5-yl)-propyl)hydrazo-6-O-methyl-3-oxoerythronolide A, 11,12-carbamate;

9-Deoxo-9-amino-11-deoxy-5-O-desosaminyl-11-(3-(3-(4-pyridin-4-yl)-(1,2,4)oxadizol-5-yl)-propyl)hydrazo-6-O-methyl-3-oxoerythronolide A, 11,12-carbamate;

9-Deoxo-9-amino-11-deoxy-5-O-desosaminyl-11-(3-benzotrizol-1-yl-propyl)hydrazo-6-O-methyl-3-oxoerythronolide A, 11,12-carbamate;

9-Deoxo-9-amino-11-deoxy-5-O-desosaminyl-11-(3-benzotrizol-2-yl-propyl)hydrazo-6-O-methyl-3-oxoerythronolide A, 11,12-carbamate;

9-Deoxo-9-amino-11-deoxy-5-O-desosaminyl-11-(3-(1H-indol-3-yl)-propyl)hydrazo-6-O-methyl-3-oxoerythronolide A, 11,12-carbamate;

9-Deoxo-9-amino-11-deoxy-5-O-desosaminyl-11-(3-pyridin-4-yl-propyl)hydrazo-6-O-methyl-3-oxoerythronolide A, 11,12-carbamate;

9-Deoxo-9-amino-11-deoxy-5-O-desosaminyl-11-(3-pyridin-3-yl-propyl)hydrazo-6-O-methyl-3-oxoerythronolide A, 11,12-carbamate;

9-Deoxo-9-amino-11-deoxy-5-O-desosaminyl-11-(3-(pyridin-2-yl-propyl)hydrazo-6-O-methyl-3-oxoerythronolide A, 11,12-carbamate;

9-Deoxo-9-amino-11-deoxy-5-O-desosaminyl-11-(3-phenylpropyl)hydrazo-6-O-methyl-3-oxoerythronolide A, 11,12-carbamate;

9-Deoxo-9-amino-11-deoxy-5-O-desosaminyl-11-(3-(2-methoxyphenyl)-propyl)hydrazo-6-O-methyl-3-oxoerythronolide A, 11,12-carbamate;

9-Deoxo-9-amino-11-deoxy-5-O-desosaminyl-11-(3-furan-2-yl-propyl)hydrazo-6-O-methyl-3-oxoerythronolide A, 11,12-carbamate;

9-Deoxo-9-amino-11-deoxy-5-O-desosaminyl-11-(3-thiophen-2-yl-propyl)hydrazo-6-O-methyl-3-oxoerythronolide A, 11,12-carbamate;

9-Deoxo-9-amino-11-deoxy-5-O-desosaminyl-11-(3-pyrrol-1-yl-propyl)hydrazo-6-O-methyl-3-oxoerythronolide A, 11,12-carbamate;

9-Deoxo-9-amino-11-deoxy-5-O-desosaminyl-11-(3-(2-pyridin-3-yl-thiazol-4-yl)-propyl)hydrazo-6-O-methyl-3-oxoerythronolide A, 11,12-carbamate;

9-Deoxo-9-amino-11-deoxy-5-O-desosaminyl-11-(3-(2-phenyl-thiazol-5-yl)-propyl)hydrazo-6-O-methyl-3-oxoerythronolide A, 11,12-carbamate;

9-Deoxo-9-amino-11-deoxy-5-O-desosaminyl-11-(3-(4-phenyl-1H-imidazol-2-yl)-propyl)hydrazo-6-O-methyl-3-oxoerythronolide A, 11,12-carbamate;

and the pharmaceutically acceptable salts of the foregoing compounds.

The invention also relates to a pharmaceutical composition for the treatment of an infection in a mammal, fish or bird which comprises a therapeutically effective amount of a compound of claim 1 and a pharmaceutically acceptable carrier.

The invention also relates to a method of treating an infection in a mammal, fish, or bird which comprises administering to said mammal, fish, or bird a therapeutically effective amount of a compound of claim 1.

The invention also relates to a method of preparing a compound of the formula I

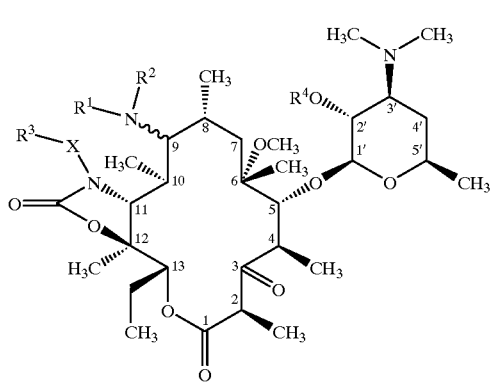

and pharmaceutically acceptable salts thereof, wherein:
X is —CR$^5$R$^6$— or —NR$^5$— or —O—;

or X is taken together with R$^3$ to form —N=CR$^7$R$^8$;

or X and R$^3$ are taken together to form a heterocyclic ring of the formula XI

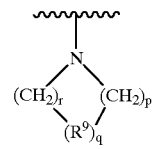

XI wherein in said ring of formula XI, r and p are each independently an integer ranging from 1 to 3, q is 0 or 1, and R$^9$ is —CH$_2$—, —O—, —S—, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents, and the nitrogen atom where R$^9$ is —NH— is optionally substituted by 1 substituent, and each hydrogen atom of R$^9$ where R$^9$ is —CH$_2$—, —CH=CH—, or —CH(OH)CH(OH) is optionally substituted by one substituent, said optional substituents being independently selected from the group consisting of —C(O)O(C$_1$–C$_{10}$ alkyl), C$_1$–C$_{10}$ alkoxy, C$_1$–C$_{10}$ alkanoyl, halo, nitro, cyano, 4–10 membered heterocyclic, C$_1$–C$_{10}$ alkyl, —NR$^5$R$^6$, C$_6$–C$_{10}$ aryl, —S(O)$_n$(C$_1$–C$_{10}$ alkyl) wherein n is an integer ranging from 0 to 2, and —SO$_2$NR$^5$R$^6$;

each R$^1$ and R$^2$ is independently selected from H and C$_1$–C$_{12}$ alkyl, wherein one or two carbons of said alkyl are optionally replaced by a heteroatom selected from O, S and N, and are optionally substituted by 1 to 3 substituents selected from the group consisting of —C(O)O(C$_1$–C$_{10}$) alkyl, —O(C$_1$–C$_{10}$)alkyl, C$_1$–C$_{10}$ alkanoyl, halo, nitro, cyano, C$_1$–C$_{10}$ alkyl, 4–10 membered heterocyclic, C$_6$–C$_{10}$ aryl, —N(C$_1$–C$_{10}$) alkyl, —S(C$_1$–C$_{10}$ alkyl), —SO(C$_1$–C$_{10}$) alkyl, —SO$_2$(C$_1$–C$_{10}$)alkyl and —SO$_2$N(C$_1$–C$_{10}$)alkyl;

or R$^1$ and R$^2$ are taken together with the nitrogen atom to which they are linked to form —N=CR$^7$R$^8$;

or R$^1$ and R$^2$ are taken together with the nitrogen atom to which they are linked to form a heterocyclic ring of the formula XI

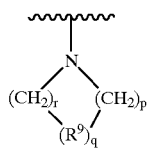

XI wherein in said ring of formula XI, r and p are each independently an integer ranging from 1 to 3, q is 0 or 1, and R$^9$ is —CH$_2$—, —O—, —S—, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents, and the nitrogen atom where R$^9$ is —NH— is optionally substituted by 1 substituent, and each hydrogen atom of R$^9$ where R$^9$ is —CH$_2$—, —CH=CH—, or —CH(OH)CH(OH) is optionally substituted by one substituent, said optional substituents being independently selected from the group consisting of —C(O)O(C$_1$–C$_{10}$ alkyl), C$_1$–C$_{10}$ alkoxy, C$_1$–C$_{10}$ alkanoyl, halo, nitro, cyano, 4–10 membered heterocyclic, C$_1$–C$_{10}$ alkyl, —NR$^5$R$^6$, C$_6$–C$_{10}$ aryl, —S(O)$_n$ ($C_1$–$C_{10}$ alkyl) wherein n is an integer ranging from 0 to 2, and —$SO_2NR^5R^6$;

$R^3$ is H, $R^7$, —C(O)$R^7$, C(O)$R^{10}$, —C(O)O$R^7$, —C(O)O$R^{10}$, or —($CR^5R^6$)$_m$$R^{10}$, wherein m is an integer ranging from 0 to 6 and both $R^5$ and $R^6$ may vary for each interation where m is greater than 1;

$R^4$ is H, —C(O)$R^{10}$ or $C_1$–$C_{18}$ alkanoyl, wherein in the alkyl portion of said alkanoyl one or two carbons optionally may be replaced by a heteroatom selected from O, S and N;

each $R^5$ and $R^6$ is independently H or $C_1$–$C_6$ alkyl;

each $R^7$ and $R^8$ is independently selected from H and $C_1$–$C_{12}$ alkyl, wherein one or two carbons of said alkyl are optionally replaced by a heteroatom selected from O, S and N, and are optionally substituted by 1 to 3 substituents selected from the group consisting of —C(O)O($C_1$–$C_{10}$) alkyl, —O($C_1$–$C_{10}$)alkyl, $C_1$–$C_{10}$ alkanoyl, halo, nitro, cyano, $C_1$–$C_{10}$ alkyl, 4–10 membered heterocyclic, $C_6$–$C_{10}$ aryl, —N($C_1$–$C_{10}$)alkyl, —S($C_1$–$C_{10}$ alkyl), —SO($C_1$–$C_{10}$) alkyl, —$SO_2$($C_1$–$C_{10}$)alkyl and —$SO_2$N($C_1$–$C_{10}$)alkyl; and $R^{10}$ is a 4–10 membered heterocyclic or $C_6$–$C_{10}$ aryl; wherein said heterocyclic and aryl groups are optionally substituted by 1 to 3 substituents independently selected from the group consisting of 4–10 membered heterocyclic, $C_6$–$C_{10}$ aryl, —NHC(O)($C_1$–$C_{10}$)alkyl, —NHC(O)N($C_1$–$C_{10}$)alkyl, —C(O)O($C_1$–$C_{10}$)alkyl, —O($C_1$–$C_{10}$)alkyl, $C_1$–$C_{10}$ alkanoyl, halo, nitro, cyano, ($C_1$–$C_{10}$) alkyl, —N($C_1$–$C_{10}$)alkyl, —S($C_1$–$C_{10}$ alkyl), —SO($C_1$–$C_{10}$) alkyl), —$SO_2$($C_1$–$C_{10}$)alkyl and —$SO_2$N($C_1$–$C_{10}$)alkyl, which comprises treating a compound of the formula II

II

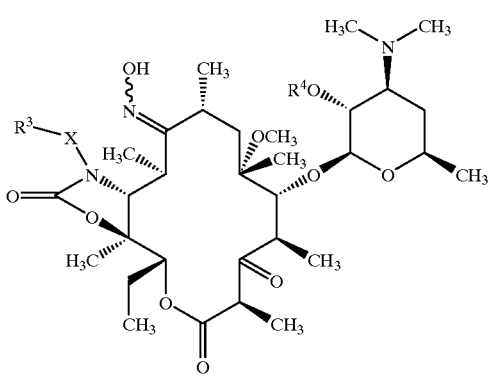

wherein X, $R^3$, and $R^4$ are as defined above, with a reducing agent.

An example of a reducing agent is titanium trichloride ($TiCl_3$). The compound of formula I can be prepared by treating a compound of the formula II with a reducing agent in a polar solvent such as methanol and ethanol. The preparation of formula I is described in U.S. patent application Ser. No. 60/049,349, filed Jun. 11, 1997 which is incorporated herein by reference in its entirety.

The term "treatment", as used herein, unless otherwise indicated, includes the treatment or prevention of a bacterial infection or protozoa infection as provided in the method of the present invention.

Patients that can be treated with the compounds of formula I, and the pharmaceutically acceptable salts thereof, include mammals (particularly humans), fish, and birds suffering from infections caused by various microorganisms including Gram positive and Gram negative bacteria.

As used herein, unless otherwise indicated, the term "bacterial infection(s)" or "protozoa infections"; includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chiamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chiamydia trachomatis, Neisseria gonorrhoeae, S. aureus, S. pneumoniae, S. pyogenes, H. influenzae,* or *Listeria* spp.; disseminated *Mycobacterlum avium* complex (MAC) disease related to infection by *Mycobacterium avium,* or *Mycobacterium intracelfulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or *Bacteroides* spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory disease related to infection by *P. haem., P. multocida, Mycoplasma bovis,* or Bordetelia spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep.*

*dysgalactiae,* Kiebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to infection by *Fusobacterium necrophorum* or *Bacteroides nodosus;* cow pink-eye related to infection by *Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius,* coagulase neg. Staph. or *P. multocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotelia. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

In the chemical structures depicted herein, a wavy line indicates that the stereochemistry at the chiral center to which the wavy line is connected is either an R or S configuration where the wavy line is connected to a carbon atom. In the compound of formula I, the wavy line at position 10 of the macrolide ring indicates that the methyl group can be either R or S configuration at that position. In the compound of formula I, the wavy line connected to the oxime nitrogen at position 9 of the macrolide ring indicates that the —OR$^1$ moiety is in an E or R$^9$ configuration.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes —C(O)-alkyl groups wherein "alkyl" is as defined above.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

As used herein, unless otherwise indicated, "Ac" indicates an acetyl group.

As used herein, unless otherwise indicated, "Me" indicates a methyl group.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula I that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula I, and pharmaceutically acceptable salts thereof, wherein the radiolabel is selected from $^3$H, $^{11}$C and $^{14}$C. Such radiolabelled compounds are useful as research or diagnostic tools.

Certain compounds of formula I may have asymmetric centers and therefore exist in different enantiomeric forms. This invention relates to the use of all optical isomers and stereoisomers of the compounds of formula I and mixtures thereof. In particular, the invention includes both the R and S configurations of the methyl group at C-10 of the macrolide ring of formula I, and both the E and R$^9$ configurations of the —OR$^1$ group connected to the nitrogen of the oxime moiety at C-9 of the macrolide ring of formula I. The compounds of formula I may also exist as tautomers. This invention relates to the use of all such tautomers and mixtures thereof.
DETAILED DESCRIPTION OF THE INVENTION
The preparation of the compounds of the present invention is illustrated in the following Schemes 1 to 3.
Scheme 1
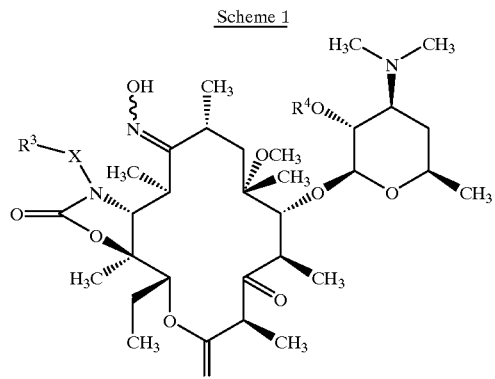
II
↓ 1
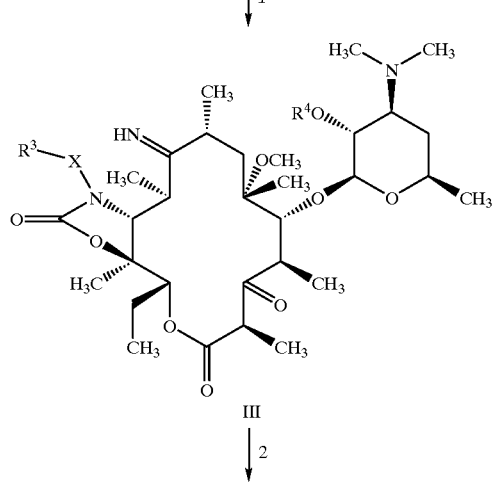
III
↓ 2
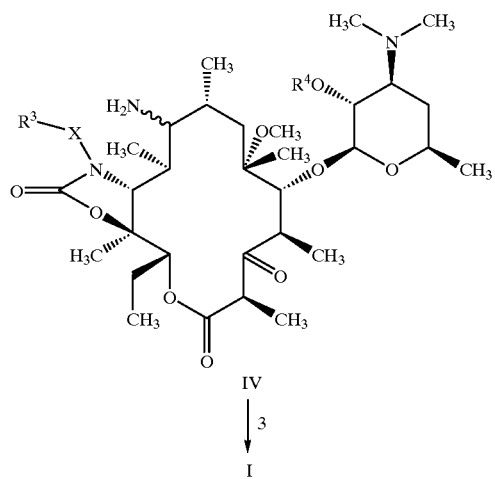
IV
↓ 3
I
Scheme 2
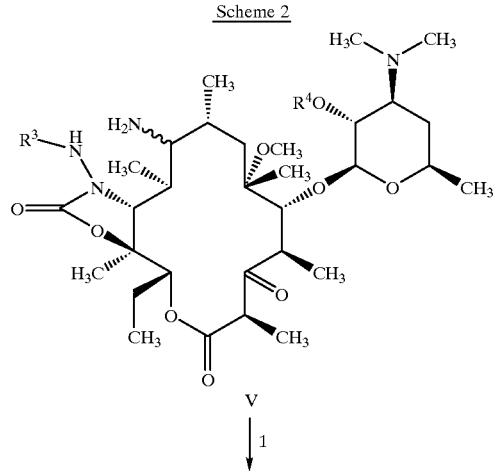
V
↓ 1
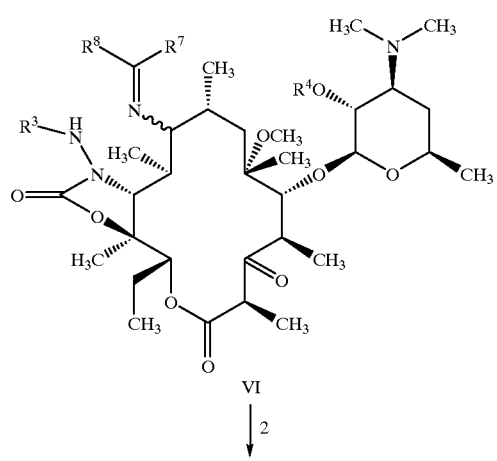
VI
↓ 2
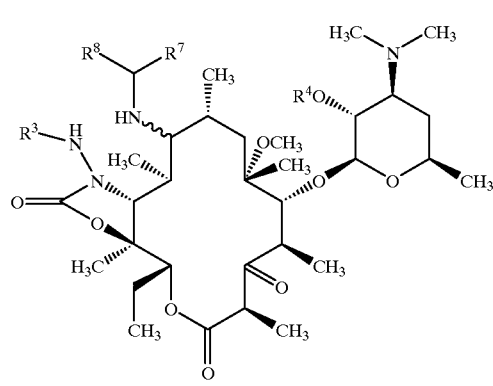
VII Scheme 3

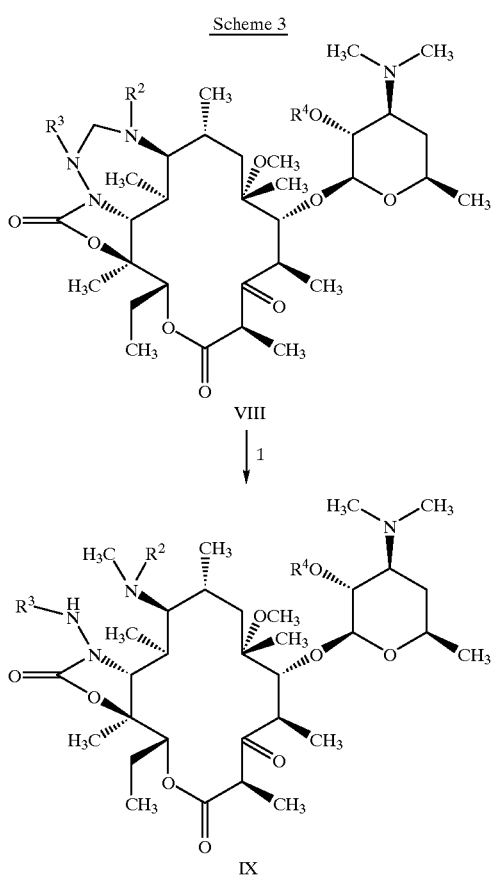

Scheme 1 illustrates the general synthesis of the compounds of the present invention. In Scheme 1, the starting compound of formula II can be prepared substantially as described in U.S. patent application Ser. No. 60/049,349 filed Jun. 11, 1997, incorporated herein by reference in its entirety. With reference to step 1 of Scheme 1, the reduction of 9-hydroxyimino group of the compound of formula II can be effected by treating the starting compound with a reducing agent such as $TiCl_3$ in a polar solvent such as methanol. The resulting imine of formula III can be converted to the corresponding amine of formula IV, as shown in step 2 of Scheme 1, by means of reduction with a reducing agent such as $NaBH_3CN$ in a polar solvent such as methanol. The resulting primary amine of formula IV can be transformed into an alkylated secondary or tertiary amine, as shown in step 4 of scheme 1, through reductive alkylation.

Step 1 of scheme 2 illustrates the general synthesis of the compounds of formula I, wherein X is NH, $R^1$ and $R^2$ together with the nitrogen atom to which they are linked form
$N=CR^7R^8$. The preparation of compounds of formula V is shown in Scheme 1, wherein X is NH. The compound of formula VI can be prepared by reacting the compound of formula V in a solvent such as ethanol or toluene with $R^7R^8C=O$, wherein $R^7$ and $R^8$ are defined as above, in the presence of an acid catalyst such as acetic acid or PTSA (para-toluenesulfonic acid), at a temperature within the range of about at 40°–80° C. for a period of about 1 to 20 hours. Step 2 of Scheme 2 illustrates the general synthesis of the compounds of formula I, wherein X is NH, $R^1$ is H, and $R^2$ is —$CH(R^7R^8)$. The compound of formula VII can be obtained from that of formula VI by means of reduction such as $NaBH_3CN$ under acidic conditions.

Scheme 3 illustrates the synthesis of the compounds of formula I, wherein X is NH, $R^1$ is Me and $R^2$, $R^3$ are defined as above. In scheme 3, the starting compound of formula VIII can be prepared as described in U.S. patent application Ser. No. 60/063161, entitled "Tricyclic Erythromycin Derivatives", (Yong-Jin Wu) filed Oct. 29, 1997. The compound of formula IX can be obtained from that of formula VIII via a reducing agent such as $NaBH_3CN$ at pH ranging from 2 to 6 in a solvent such as methanol or acetonitrile.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula I that are acidic in nature, are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantifies of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibacterial assay is performed in microtiter trays and interpreted according to *Performance Standards for Antimicrobial Disk Susceptibility Tests—Sixth Edition; Approved Standard,* published by The National Committee for Clinical Laboratory Standards (NCCLS) guidelines; the minimum inhibitory concentration (MIC) is used to compare strains. acr AB or acr AB-like indicates that an intrinsia multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | mefA |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Haemophilus influenzae* 0085 | susceptible; acr AB-like |
| *Haemophilus influenzae* 0131 | susceptible; acr AB-like |
| *Moraxella catarrhalis* 0040 | susceptible |
| *Moraxella catarrhalis* 1055 | erythromycin intermediate resistance |
| *Escherichia coli* 0266 | susceptible; acr AB |
| *Haemophilus influenzae* 1100 | susceptible; acr AB-like |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemofytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. multocida* strain 59A006) intraperitoneally. Each experiment has at least 3 non-medicated control groups including one infected with 0.1X challenge dose and two infected with 1X challenge dose; a 10X challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The P. multocida model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula I, and the pharmaceutically acceptable salts thereof (hereinafter "the active compounds"), may be administered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The Examples provided below illustrate specific embodiments of the invention, but the invention is not limited in scope to the Examples specifically exemplified.

EXAMPLE 1

9-deoxo-9-imino-11-deoxy-5-O-desosaminyl-11-(3-quinolin-4-yl-propyl)hydrazo-6-O-methyl-3-oxoerythronolide A, 11,12-carbamate (formula III, X=NH, $R^4$=H, $R^3$=3-quinolin-4-yl-propyl)

To a solution of 9-deoxo-9-hydroxyimino-11-deoxy-5-O-desosaminyl-11-(3-quinolin-4-yl-propyl)hydrazo-4-O- methyl-3-oxoerythronolide A, 11,12-carbamate (949 mg, 1.2 mmol) and NH$_4$OAc (949 mg) in methanol (11 mL) at room temperature was added TiCl$_3$ (1.47M in 20% HCl, 5.10 mL) dropwise over a period of 40 minutes via a syringe drive. The reaction solution was stirred at room temperature for 3 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to afford the title compound as a white solid.

MS: m/z 797 (M+H).

EXAMPLE 2

9-Deoxo-9-amino-11-deoxy-5-O-desosaminyl-11-(3-quinolin-4-yl-propyl)hydrazo-6-O-methyl-3-oxoerythronolide A, 11,12-carbamate (formula IV, X=NH, R$^4$=H, R$^3$=3-quinolin-4-yl-propyl)

To a solution of 9-deoxo-9-imino-11-deoxy-5-O-desosaminyl-11-(3-quinolin-4-yl-propyl)hydrazo-6-O-methyl-3-oxoerythronolide A, 11,12-carbamate, prepared as above, in methanol (11 mL) at room temperature was added NaBH$_3$CN (1.1 g, 17.53 mmol) followed by HOAc(1.0 ml, 17.53 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative (TLC) (89% CH$_2$Cl$_2$-9% MeOH-1% NH$_3$•H$_2$O) to afford the title compound as a white solid.

Exact mass calcd. for C$_{43}$H$_{68}$N$_5$O$_9$ (M+H): 798.5017; found: 798.5028.

EXAMPLE 3

9-deoxo-9-imino-11-deoxy-5-O-desosaminyl-11-(3-phenylpropyl)hydrazo-6-O-methyl-3-oxoerythronolide A, 11,12-carbamate (formula III, X=NH, R$^4$=H, R$^3$=3-phenylpropyl)

To a solution of 9-deoxo-9-hydroxyimino-11-deoxy-5-O-desosaminyl-11-(3-phenylpropyl)hydrazo-6-O-methyl-3-oxoerythronolide A, 11,12-carbamate (20 mg, 0.03 mmol) and NH$_4$OAc (20 mg) in methanol (0.25 mL) at room temperature was added TiCl$_3$ (1.47M in 20% HCl, 79 μL) dropwise over a period of 40 minutes via a syringe drive. The reaction solution was stirred at room temperature for 10 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to afford the title compound as a white solid.

MS: m/z 746 (M+H).

EXAMPLE 4

9-Deoxo-9-amino-11-deoxy-5-O-desosaminyl-11-(3-phenylpropyl)hydrazo-6-O-methyl-3-oxoerythronolide A, 11,12-carbamate (formula IV, X=NH, R$^4$=H, R$^3$=phenylpropyl)

To a solution of 9-deoxo-9-imino-11-deoxy-5-O-desosaminyl-11-(3-phenylpropyl)hydrazo-6-O-methyl-3-oxoerythronolide A, 11,12-carbamate, prepared as above, in methanol (0.2 mL) at room temperature was added NaBH$_3$CN (25 mg, 0.40 mmol) followed by HOAc( 23 μl, 0.40 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (8 mg).

MS: m/z 748 (M+H).

EXAMPLE 5

9-Deoxo-9-imino-11-deoxy-5-O-desosaminyl-11-(3-(4-phenyl-imidazol-1-yl)-propyl)hydrazo-6-O-methyl-3-oxoerythronolide A, 11,12-carbamate (formula III, X=NH, R$^4$=H, R$^3$=3-(4-phenyl-imidazol-1-yl-propyl)

To a solution of 9-deoxo-9-hydroxyimino-11-deoxy-5-O-desosaminyl-11-(3-(4-phenyl-imidazol-1-yl)-propyl) hydrazo-6-O-methyl-3-oxoerythronolide A, 11,12-carbamate (30 mg, 0.04 mmol) and NH$_4$OAc (30 mg) in methanol (0.40 mL) at room temperature was added TiCl$_3$ (1.47M in 20% HCl, 150 μL) dropwise over a period of 40 min via a syringe drive. The reaction solution was stirred at room temperature for 10 h. Sat. NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to afford the title compound as a white solid.

MS: m/z 812 (M+H).

EXAMPLE 6

9-Deoxo-9-amino-11-deoxy-5-O-desosaminyl-11-(3-(4-phenyl-imidazol-1-yl)-propyl)hydrazo-6-O-methyl-3-oxoerythronolide A, 11,12-carbamate (formula IV, X=NH, R$^4$=H, R$^3$=3-(4-phenyl-imidazol-1-yl-propyl)

To a solution of 9-deoxo-9-imino-11-deoxy-5-O-desosaminyl-11-(3-(4-phenyl-imidazol-1-yl)-propyl) hydrazo-6-O-methyl-3-oxoerythronolide A, 11,12-carbamate, prepared as above, in methanol (0.4 mL) at room temperature was added NaBH$_3$CN (34 mg, 0.54 mmol) followed by HOAc( 23 μl, 0.40 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (13 mg).

MS: m/z 814 (M+H).

EXAMPLE 7

9-Deoxo-9-imino-11-deoxy-5-O-desosaminyl-11-(3-benzoimidazol-1-yl-propyl)hydrazo-6-O-methyl-3-oxoerythronolide A, 11,12-carbamate (formula III, X=NH, R$^4$=H, R$^3$=3-benzoimidazol-1-yl-propyl)

To a solution of 9-deoxo-9-hydroxyimino-11-deoxy-5-O-desosaminyl-11-3-benzoimidazol-1-yl-propyl)hydrazo-6-O-methyl-3-oxoerythronolide A, 11,12-carbamate (40 mg, 0.04 mmol) and NH$_4$OAc (40 mg) in methanol (0.50 mL) at room temperature was added TiCl$_3$ (1.47M in 20% HCl, 204 μL) dropwise over a period of 40 min via a syringe drive.

The reaction solution was stirred at room temperature for 10 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to afford the title compound as a white solid.

MS: m/z 785 (M+H).

EXAMPLE 8

9-Deoxo-9-amino-11-deoxy-5-O-desosaminyl-11-(3-benzoimidazol-1-yl-propyl)-1-yl)-propyl)hydrazo-6-O-methyl-3-oxoerythronolide A, 11,12-carbamate (formula IV, X=NH, R$^4$=H, R$^3$=3-benzoimidazol-1-yl-propyl)

To a solution of 9-deoxo-9-imino-11-deoxy-5-O-desosaminyl-11-(3-(4-phenyl-imidazol-1-yl-propyl)hydrazo-6-O-methyl-3-oxoerythronolide A, 11,12-carbamate, prepared as above, in methanol (0.5 mL) at room temperature was added NaBH$_3$CN (47 mg, 0.75 mmol) followed by HOAc( 43 µl, 0.75 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (13 mg).

MS: m/z 787 (M+H).

EXAMPLE 9

9-Deoxo-9-imino-11-deoxy-5-O-desosaminyl-11-(3-indol-1-yl-propyl)hydrazo-6-O-methyl-3-oxoerythronolide A, 11,12-carbamate (formula III, X=NH, R$^4$=H, R$^3$=3-indol-1-yl-propyl)

To a solution of 9-deoxo-9-hydroxyimino-11-deoxy-5-O-desosaminyl-11-(3-indol-1-yl-propyl)hydrazo-6-O-methyl-3-oxoerythronolide A, 11,12-carbamate (30 mg, 0.04 mmol) and NH$_4$OAc (30 mg) in methanol (0.50 mL) at room temperature was added TiCl$_3$ (1.47M in 20% HCl, 150 µL) dropwise over a period of 40 min via a syringe drive. The reaction solution was stirred at room temperature for 10 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to afford the title compound as a white solid.

MS: m/z 784 (M+H).

EXAMPLE 10

9-Deoxo-9-amino-11-deoxy-5-O-desosaminyl-11-(3-indol-1-yl-propyl)hydrazo-6-O-methyl-3-oxoerythronolide A, 11,12-carbamate (formula IV, X=NH, R$^4$=H, R$^3$=3-indol-1-yl-propyl)

To a solution of 9-deoxo-9-imino-11-deoxy-5-O-desosaminyl-11-(3-indol-1-yl-propyl)hydrazo-6-O-methyl-3-oxoerythronolide A, 11,12-carbamate, prepared as above, in methanol (0.5 mL) at room temperature was added NaBH$_3$CN (35 mg, 0.56 mmol) followed by HOAc (32 µl, 0.56 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (5 mg).

MS: m/z 786 (M+H)

EXAMPLE 11

9-deoxo-9-imino-11-deoxy-5-O-desosaminyl-11-(3-(4-pyridin-3-yl-imidazol-1-yl)-propyl)hydrazo-6-O-methyl-3-oxoerythronolide A, 11,12-carbamate (formula III, X=NH, R$^4$=H, R=3-quinolin4-yl-propyl)

To a solution of 9-deoxo-9-hydroxyimino-11-deoxy-5-O-desosaminyl-11-(3-(4-pyridin-3-yl-imidazol-1-yl)-propyl)hydrazo-6-O-methyl-3-oxoerythronolide A, 11,12-carbamate (291 mg, 0.35 mmol) and NH$_4$OAc (290 mg) in methanol (3.2 mL) at room temperature was added TiCl$_3$ (1.47M in 20% HCl, 3.6 mL) dropwise over a period of 40 minutes via a syringe drive. The reaction solution was stirred at room temperature for 3 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to afford the title compound as a white solid.

MS: m/z 812 (M+H).

EXAMPLE 12

9-Deoxo-9-amino-11-deoxy-5-O-desosaminyl-11-(3-(4-pyridin-3-yl-imidazol-1-yl)-propyl)hydrazo-6-O-methyl-3-oxoerythronolide A, 11,12-carbamate (formula IV, X=NH, R$^4$=H, R$^3$=3-quinolin4-yl-propyl)

To a solution of 9-deoxo-9-imino-11-deoxy-5-O-desosaminyl-11-(3-(4-pyridin-3-yl-imidazol-1-yl)-propyl)hydrazo-6-O-methyl-3-oxoerythronolide A, 11,12-carbamate from Example 11, in methanol (3.2 mL) at room temperature was added NaBH$_3$CN (330 mg, 5.25 mmol) followed by HOAc (0.30 ml, 5.25 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative (TLC) (89% CH$_2$Cl$_2$-9% MeOH-1% NH$_3$•H$_2$O) to afford the title compound as a white solid.

MS: m/z 814 (M+H).

EXAMPLE 13

Compound of formula VI, R$^4$=H, R$^3$=3-quinolin-4-yl-propyl, R$^7$=R$^8$=Me

To a solution of 9-deoxo-9-amino-11-deoxy-5-O-desosaminyl-11-(3-quinolin4-yl-propyl)hydrazo-6-O-methyl-3-oxoerythronolide A, 11,12-carbamate from Example 2 (30 mg, 0.04 mmol), in acetone (1.0 mL) at room temperature was added HOAc (28 µl, 0.49 mmol). The resulting solution was heated under reflux for 6 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give title compound as a solid (36 mg).

MS: m/z 839 (M+H)

EXAMPLE 14

Compound of formula VII, $R^4$=H, $R^3$=3quinolin-4-yl-propyl, $R^7$=$R^8$=Me

To a solution of the compound from Example 13 (30 mg, 0.04 mmol), in MeOH (1.0 mL) at room temperature was added HOAc (33 µl, 0.57 mmol) and NaBH$_3$CN (23 mg, 0.36 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (5 mg).

MS: m/z 841 (M+H)

EXAMPLE 15

Compound of formula VI, $R^4$=H, $R^3$=3-quinolin4-yl-propyl, $R^7$=H, $R^8$=C$_2$H$_5$ To a solution of 9-deoxo-9-amino-11-deoxy-5-O-desosaminyl-11-(3-quinolin-4-yl-propyl)hydrazo-6-O-methyl-3-oxoerythronolide A, 11,12-carbamate from Example 2 (150 mg, 0.19 mmol), in MeOH (2.0 mL) at room temperature was added propionaldehyde (0.15 mL, 2.1 mmol). The resulting solution was heated at 65° C. for 6 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give title compound as a solid (150 mg).

MS: m/z 839 (M+H)

EXAMPLE 16

Compound of formula VII, $R^4$=H, $R^3$=3-quinolin4-yl-propyl, $R^7$=H, $R^8$=C$_2$H$_5$ To a solution of the compound from Example 15 (150 mg, 0.19 mmol), in MeOH (2.0 mL) at room temperature was added HOAc(161 µl, 2.8 mmol) and NaBH$_3$CN (177 mg, 2.8 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give the title compound as a white solid (150 mg).

MS: m/z 841 (M+H)

EXAMPLE 17

Compound of formula VI, $R^4$=H, $R^3$=3-quinolin-4-yl-propyl, $R^7$=H, $R^8$=Me To a solution of 9-deoxo-9-amino-11-deoxy-5-O-desosaminyl-11-(3-quinolin-4-yl-propyl)hydrazo-6-O-methyl-3-oxoerythronolide A, 11,12-carbamate from Example 2 (150 mg, 0.19 mmol), in MeOH (2.0 mL) at room temperature was added acetaldehyde (0.12 mL, 2.1 mmol). The resulting solution was heated at 65° C. for 6 hours. Saturated NaHCO, was added followed by CH$_2$Cl$_2$, the organic layer was separated, and the aqueous layer was extracted with CH$_2$Cl$_2$. The combined organic layers were washed with brine, dried over MgSO$_4$, and concentrated to give title compound as a solid (150 mg).

MS: m/z 825 (M+H)

EXAMPLE 18

Compound of formula VII, $R^4$=H, $R^3$=3-quinolin4-yl-propyl, $R^7$=H, $R^3$=Me To a solution of the compound from Example 17 (150 mg, 0.19 mmol), in MeOH (2.0 mL) at room temperature was added HOAc(161 µl, 2.8 mmol) and NaBH$_3$CN (177 mg, 2.8 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give the title compound as a white solid (156 mg).

MS: m/z 827 (M+H)

EXAMPLE 19

Compound of formula IX, $R^4$=$R^2$=H, $R^3$=3-quinolin-4-yl-propyl

To a solution of the compound of formula VII, $R^4$=$R^2$=H, $R^3$=3-quinolin-4-yl-propyl, (30 mg, 0.04 mmol), in MeCN (0.20 mL) and 0.05M potassium biphthalate buffer (0.20 mL) at room temperature was added 1N aqueous HCl until the pH was adjusted to 6. NaBH$_3$CN (16 mg) was added and the resulting solution was stirred at room temperature for 20 h. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (8 mg).

MS: m/z 813 (M+H)

EXAMPLE 20

Compound of formula VI, $R^4$=H, $R^3$=3-(4-phenyl-imidazol-1-yl)-propyl, $R^7$=H, $R^8$=Me To a solution of 9-deoxo-9-amino-11-deoxy-5-O-desosaminyl-11-(3-(4-phenyl-imidazol-1-yl)-propyl) hydrazo-6-O-methyl-3-oxoerythronolide A, 11,12-carbamate from Example 6 (150 mg, 0.19 mmol), in CHCl$_3$ (2.0 mL) at room temperature was added acetaldehyde (0.13 mL, 2.1 mmol). The resulting solution was heated at 60° C. for 1 hour. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give title compound as a solid (150 mg).

MS: m/z 839 (M+H)

EXAMPLE 21

Compound of formula VII, $R^4$=H, $R^3$=3-(4-phenyl-imidazol-1-yl)-propyl, $R^7$=H, $R^8$=Me To a solution of the compound from Example 20 (150 mg, 0.19 mmol), in MeOH (2.0 mL) at room temperature was added HOAc (0.17 mL) and NaBH$_3$CN (116 mg). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-

9% MeOH-1% NH$_3$•H$_2$O) to afford the title compound as a white solid (59 mg).

MS: m/z 842 (M+H)

EXAMPLE 22

Compound of formula IX, R$^4$=R$^2$=H, R$^3$=3-(4-phenyl-imidazol-1-yl)-propyl

To a solution of the compound of formula VIII, R$^4$=R$^2$=H, R$^3$=3-(4-phenyl-imidazol-1-yl)-propyl, (300 mg, 0.36 mmol), in MeCN (2.0 mL) and 0.05M potassium biphthalate buffer (2.0 mL) at room temperature was added 1N aqueous HCl until the pH was adjusted to 6. NaBH$_3$CN (160 mg) was added and the resulting solution was stirred at room temperature for 20 h. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (90 mg).

MS: m/z 827 (M+H)

EXAMPLE 23

Compound of formula VII, R$^4$=H, R$^3$=3-phenylpropyl, R$^7$=H, R$^8$=Me

To a solution of 9-deoxo-9-amino-11-deoxy-5-O-desosaminyl-11-phenylpropyl)hydrazo-6-O-methyl-3-oxoerythronolide A, 11,12-carbamate from Example 4 (150 mg, 0.20 mmol), in MeOH (2.0 mL) at room temperature was added acetaldehyde (0.12 mL, 2.1 mmol). The resulting solution was heated at 65° C. for 1 hour. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give title compound as a solid (150 mg).

MS: m/z 774 (M+H)

EXAMPLE 24

Compound of formula VII, R$^4$=H, R$^3$=3-phenylpropyl, R$^7$=H, R$^8$=Me

To a solution of the compound from Example 23 (150 mg), in MeOH (2.0 mL) at room temperature was added HOAc(0.17 mL, 2.8 mmol) and NaBH$_3$CN (177 mg, 3.0 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (70 mg).

MS: m/z 776 (M+H)

EXAMPLE 25

Compound of formula VI, R$^4$=H, R$^3$=3-phenylpropyl, R$^7$=H, R$^8$=Et

To a solution of 9-deoxo-9-amino-11-deoxy-5-O-desosaminyl-11-phenylpropyl)hydrazo-6-O-methyl-3-oxoerythronolide A, 11,12-carbamate from Example 4 (150 mg, 0.20 mmol), in MeOH (2.0 mL) at room temperature was added propionaldehyde (0.16 mL, 2.1 mmol). The resulting solution was heated at 65° C. for 1 hour. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated to give title compound as a solid (150 mg).

MS: m/z 788 (M+H)

EXAMPLE 26

Compound of formula VII, R$^4$=H, R$^3$=3-phenylpropyl, R$^7$=H, R$^8$=Et

To a solution of the compound from Example 25 (150 mg), in MeOH (2.0 mL) at room temperature was added HOAc(0.17 mL, 2.8 mmol) and NaBH$_3$CN (177 mg, 3.0 mmol). The resulting solution was stirred at room temperature for 12 hours. Saturated NaHCO$_3$ was added followed by CH$_2$Cl$_2$, the organic layer was separated, and the aqueous layer was extracted with CH$_2$Cl$_2$. The combined organic layers were washed with brine, dried over MgSO$_4$, and concentrated. The residue was purified by preparative TLC (89% CH$_2$Cl$_2$-9% MeOH-1% NH$_3$•H$_2$O) to afford the title compound as a white solid (65 mg).

MS: m/z 790 (M+H)

What is claimed is:

1. A compound of the formula I

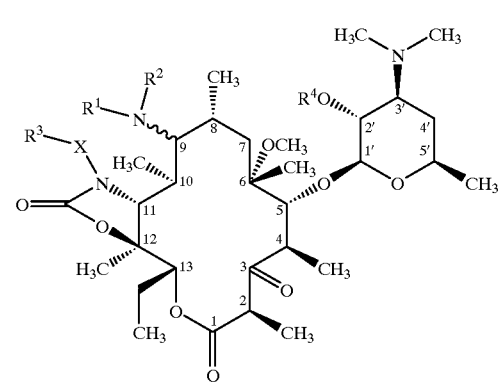

or a pharmaceutically acceptable salt thereof, wherein:

X is —CR$^5$R$^6$— or —NR$^5$— or —O—;

or X is taken together with R$^3$ to form —N=CR$^7$R$^8$;

or X and R$^3$ are taken together to form a heterocyclic ring of the formula XI

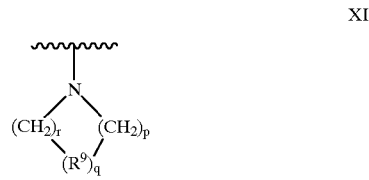

wherein in said ring of formula XI, r and p are each independently an integer ranging from 1 to 3, q is 0 or 1, and R$^9$ is —CH$_2$—, —O—, —S—, —C(O)—, —C(S)—, —SO$_2$—, —CH=CH—, —CH(OH)CH(OH)—, or —NH—; and wherein the (CH$_2$)$_r$ and (CH$_2$)$_p$ portions of said ring of formula XI are optionally substituted by 1 to 4 substituents, and the nitrogen atom where R$^9$ is —NH— is optionally substituted by 1 substituent, and each hydrogen atom of $R^9$ where $R^9$ is —$CH_2$—, —CH=CH—, or —CH(OH)CH(OH) is optionally substituted by one substituent, said optional substituents being independently selected from the group consisting of —C(O)O($C_1$–$C_{10}$ alkyl), $C_1$–$C_{10}$ alkoxy, $C_1$–$C_{10}$ alkanoyl, halo, nitro, cyano, 4–10 membered heterocyclic, $C_1$–$C_{10}$ alkyl, —$NR^5R^6$, $C_6$–$C_{10}$ aryl, —S(O)$_n$ ($C_1$–$C_{10}$ alkyl) wherein n is an integer ranging from 0 to 2, and —$SO_2NR^5R^6$;

each $R^1$ and $R^2$ is independently selected from the group consisting of H and $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)O($C_1$–$C_{10}$)alkyl, —O($C_1$–$C_{10}$)alkyl, $C_1$–$C_{10}$ alkanoyl, halo, nitro, cyano, $C_1$–$C_{10}$ alkyl, 4–10 membered heterocyclic, $C_6$–$C_{10}$ aryl, —N($C_1$–$C_{10}$) alkyl, —S($C_1$–$C_{10}$ alkyl), —SO($C_1$–$C_{10}$)alkyl, —$SO_2$($C_1$–$C_{10}$)alkyl and —$SO_2N$($C_1$–$C_{10}$)alkyl;

or $R^1$ and $R^2$ are taken together with the nitrogen atom to which they are linked to form —N=$CR^7R^8$;

or $R^1$ and $R^2$ are taken together with the nitrogen atom to which they are linked to form a heterocyclic ring of the formula XI

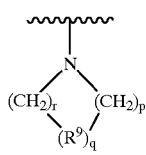

XI wherein in said ring of formula XI, r and p are each independently an integer ranging from 1 to 3, q is 0 or 1, and $R^9$ is —$CH_2$—, —O—, —S—, —C(O)—, —C(S)—, —$SO_2$—, —CH=CH—, —CH(OH)CH(OH)—, or —NH—; and wherein the $(CH_2)_r$ and $(CH_2)_p$ portions of said ring of formula XI are optionally substituted by 1 to 4 substituents, and the nitrogen atom where $R^9$ is —NH— is optionally substituted by 1 substituent, and each hydrogen atom of $R^9$ where $R^9$ is —$CH_2$—, —CH=CH—, or —CH(OH)CH(OH) is optionally substituted by one substituent, said optional substituents being independently selected from the group consisting of —C(O)O($C_1$–$C_{10}$ alkyl), $C_1$–$C_{10}$ alkoxy, $C_1$–$C_{10}$ alkanoyl, halo, nitro, cyano, 4–10 membered heterocyclic, $C_1$–$C_{10}$ alkyl, —$NR^5R^6$, $C_6$–$C_{10}$ aryl, —S(O)$_n$ ($C_1$–$C_{10}$ alkyl) wherein n is an integer ranging from 0 to 2, and —$SO_2NR^5R^6$;

$R^3$ is H, $R^7$, —C(O)$R^7$, C(O)$R^{10}$, —C(O)O$R^7$, —C(O)O$R^{10}$, or —$(CR^5R^6)_mR^{10}$, wherein m is an integer ranging from 0 to 6 and both $R^5$ and $R^6$ may vary for each interation where m is greater than 1;

$R^4$ is H, —C(O)$R^{10}$ or $C_1$–$C_{18}$ alkanoyl, wherein in the alkyl portion of said alkanoyl one or two carbons optionally may be replaced by a heteroatom selected from the group consisting of O, S and N;

each $R^5$ and $R^6$ is independently H or $C_1$–$C_6$ alkyl;

each $R^7$ and $R^8$ is independently selected from H and $C_1$–$C_{12}$ alkyl, wherein one or two carbons of said alkyl are optionally replaced by a heteroatom selected from the group consisting of O, S and N, and are optionally substituted by 1 to 3 substituents selected from the group consisting of —C(O)O($C_1$–$C_{10}$)alkyl, —O($C_1$–$C_{10}$)alkyl, $C_1$–$C_{10}$ alkanoyl, halo, nitro, cyano, $C_1$–$C_{10}$ alkyl, 4–10 membered heterocyclic, $C_6$–$C_{10}$ aryl, —N($C_1$–$C_{10}$)alkyl, —S($C_1$–$C_{10}$) alkyl), —SO($C_1$–$C_{10}$)alkyl, —$SO_2$($C_1$–$C_{10}$)alkyl and —$SO_2N$($C_1$–$C_{10}$)alkyl; and $R^{10}$ is a 4–10 membered heterocyclic or $C_6$–$C_{10}$ aryl; wherein said heterocyclic and aryl groups are optionally substituted by 1 to 3 substituents independently selected from the group consisting of 4–10 membered heterocyclic, $C_6$–$C_{10}$ aryl, —NHC(O)($C_1$–$C_{10}$)alkyl, —NHC(O)N($C_1$–$C_{10}$)alkyl, —C(O)O($C_1$–$C_{10}$)alkyl, —O—($C_1$–$C_{10}$)alkyl, $C_1$–$C_{10}$ alkanoyl, halo, nitro, cyano, ($C_1$–$C_{10}$) alkyl, —N($C_1$–$C_{10}$)alkyl, —S($C_1$–$C_{10}$ alkyl), —SO($C_1$–$C_{10}$)alkyl), —$SO_2$($C_1$–$C_{10}$)alkyl and —$SO_2N$($C_1$–$C_{10}$)alkyl.

2. The compound of claim 1 wherein $R^4$ is H.

3. The compound of claim 1 wherein X is —NH—.

4. The compound of claim 3 wherein $R^1$ is H.

5. The compound of claim 4 wherein $R^2$ is H, methyl, ethyl, isopropyl, propyl, or cyclopropyl.

6. The compound of claim 2 wherein $R^2$ is H, methyl, ethyl, isopropyl, propyl, or cyclopropyl.

7. The compound of claim 2 wherein $R^3$ is $(CH_2)_mR^{10}$ wherein m is an integer ranging from 0 to 6 and $R^{10}$ is as defined in claim 1.

8. The compound of claim 7 wherein $R^{10}$ is a 4–10 membered heterocyclic.

9. The compound of claim 8 wherein $R^{10}$ is quinolinyl, 4-phenyl-1-imidazol-1-yl, imidazo(4,5-b)pyridin-3-yl, or 4-pyridin-3-yl-imidazol-1-yl.

10. The compound of claim 1 wherein said compound is selected from the group consisting of:

9-Deoxo-9-amino-11-deoxy-5-O-desosaminyl-11-(3-quinolin-4-yl-propyl)hydrazo-6-O-methyl-3-oxoerythronolide A, 11,12-carbamate;

9-Deoxo-9-methylamino-11-deoxy-5-O-desosaminyl-11-(3-quinolin-4-yl-propyl)hydrazo-6-O-methyl-3-oxoerythronolide A, 11,12-carbamate;

9-Deoxo-9-ethylamino-11-deoxy-5-O-desosaminyl-11-(3-quinolin-4-yl-propyl)hydrazo-6-O-methyl-3-oxoerythronolide A, 11,12-carbamate;

9-Deoxo-9-propylamino-11-deoxy-5-O-desosaminyl-11-(3-quinolin-4-yl-propyl)hydrazo-6-O-methyl-3-oxoerythronolide A, 11,12-carbamate;

9-Deoxo-9-isopropylamino-11-deoxy-5-O-desosaminyl-11-(3-quinolin-4-yl-propyl)hydrazo-6-O-methyl-3-oxoerythronolide A, 11,12-carbamate;

9-Deoxo-9-cyclopropylamino-11-deoxy-5-O-desosaminyl-11-(3-quinolin-4-yl-propyl)hydrazo-6-O-methyl-3-oxoerythronolide A, 11,12-carbamate;

9-Deoxo-9-amino-11-deoxy-5-O-desosaminyl-11-(3-(7-methoxy-quinolin-4-yl)-propyl)hydrazo4-O-methyl-3-oxoerythronolide A, 11,12-carbamate;

9-Deoxo-9-amino-1-deoxy-5-O-desosaminyl-11-(3-benzoimidazol-1-yl-propyl)hydrazo-6-O-methyl-3-oxoerythronolide A, 11,12-carbamate;

9-Deoxo-9-amino-11-deoxy-5-O-desosaminyl-11-(3-indol-1-yl-propyl)hydrazo-6-O-methyl-3-oxoerythronolide A, 11,12-carbamate;

9-Deoxo-9-amino-11-deoxy-5-O-desosaminyl-11-(3-indazol-1-yl-propyl)hydrazo-6-O-methyl-3-oxoerythronolide A, 11,12-carbamate;

9-Deoxo-9-amino-11-deoxy-5-O-desosaminyl-11-(3-carbazol-1-yl-propyl)hydrazo-6-O-methyl-3-oxoerythronolide A, 11,12-carbamate;

9-Deoxo-9-amino-11deoxy-5-O-desosaminyl-11-(3-(5-phenyl-1H-pyrrol-2-yl)-propyl)hydrazo-6-O-methyl-3-oxoerythronolide A, 11,12-carbamate;

9-Deoxo-9-amino-11-deoxy-5-O-desosaminyl-1-(3-(4-phenyl-imidazol-1-yl)-propyl)hydrazo-6-O-methyl-3-oxoerythronolide A, 11,12-carbamate;

9-Deoxo-9-methylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-ethylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-propylamino-11deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-isopropylamino-11-deoxy-5-O-desosaminyl-11-(3-(4-phenyl-imidazol-1-yl)-propyl)hydrazo-6-O-methyl-3-oxoerythronolide A, 11,12-carbamate;

9-Deoxo-9-cyclopropylamino-11-deoxy-5-O-desosaminyl-11-(3-(4-phenyl-imidazol-1-yl)-propyl)hydrazo6-O-methyl-3-oxoerythronolide A, 11,12-carbamate;

9-Deoxo-9-amino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-methylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-ethylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-propylamino-11-deoxy-5-O-desosaminyl-11-(3-imidazol(4,5-b)pyridin-3-yl)-propyl)hydrazo-6-O-methyl-3-oxoerythronolide, 11,12-carbamate;

9-Deoxo-9-isopropylamino-11-deoxy-5-O-desosaminyl-11-(3-imidazol(4,5-b)pyridin-3-yl)-propyl)hydrazo-6-O-methyl-3-oxoerythronolide A, 11,12-carbamate;

9-Deoxo-9-cyclopropylamino-1-deoxy-5-desosaminyl-1-(pyridin-3-imidazol(4,5-b) -yl)-propyl)hydrazo-6-O-methyl-3-oxoerythronolide A, 11,12-carbamate;

9-Deoxo-9-amino-11- deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-methylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-ethylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-propylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-isopropylamino-11-deoxy-5-O-desosaminyl-11-(3-(4-pyridin-3-yl-imidazol-11-yl)-propyl)hydrazo-6-O-methyl-3-oxoerythronolide A, 11,12-carbamate;

9-Deoxo-9-cyclopropylamino-11-deoxy-5-O-desosaminyl-11-(3-(4-pyridin-3-yl-imidazol-1-yl)-propyl)hydrazo-6-O-methyl-3-oxoerythronolide A, 11,12-carbamate;

9-Deoxo-9-amino-11-deoxy-5-O-desosaminyl-11-(3-(3-(4-chlorophenyl)-(1,2,4)oxadizol-5-yl)-propyl)hydrazo-6-O-methyl-3-oxoerythronolide A, 11,12-carbamate;

9-Deoxo-9-amino-11-deoxy-5-O-desosaminyl-11-(3-(3-(4-methoxyphenyl)-(1,2,4)oxadizol-5-yl)-propyl)hydrazo-6-O-methyl-3-oxoerythronolide A, 11,12-carbamate;

9-Deoxo-9-amino-11-deoxy-5-O-desosaminyl-11-(3-(3-(4-pyridin4-yl)-(1,2,4)oxadizol-5-5yl)-propyl)hydrazo-6-O-methyl-3-oxoerythronolide A, 11,12-carbamate;

9-Deoxo-9-amino-11-deoxy-5-O-desosaminyl-11-(3-benzotrizol-1-yl-propyl)hydrazo-6-O-methyl-3-oxoerythronolide A, 11,12-carbamate;

9-Deoxo-9-amino-11-deoxy-5-O-desosaminyl-11-(3-benzotrizol-2-yl-propyl)hydrazo-6-O-methyl-3-oxoerythronolide A, 11,12-carbamate;

9-Deoxo-9-amino-11-deoxy-5-O-desosaminyl-11-(3-(1H-indol-3-yl)-propyl)hydrazo-6-O-methyl-3-oxoerythronolide A, 11,12-carbamate;

9-Deoxo-9-amino-11-deoxy-5-O-desosaminyl-11-(3-pyridin-4-yl-propyl)hydrazo-6-O-methyl-3-oxoerythronolide A, 11,12-carbamate;

9-Deoxo-9-amino-11-deoxy-5-O-desosaminyl-11-(3-pyridin-3-yl-propyl)hydrazo-6-O-methyl-3-oxoerythronolide A, 11,12-carbamate;

9-Deoxo-9-amino-11-deoxy-5-O-desosaminyl-11-(3-(pyridin-2-yl-propyl)hydrazo-6-O-methyl-3-oxoerythronolide A, 11,12-carbamate;

9-Deoxo-9-amino-11-deoxy-5-O-desosaminyl-11-(3-phenylpropyl)hydrazo-6-O-methyl-3-oxoerythronolide A, 11,12-carbamate;

9-Deoxo-9-amino-11-deoxy-5-O-desosaminyl-11-(3-(2-methoxyphenyl)-propyl)hydrazo-6-O-methyl-3-oxoerythronolide A, 11,12-carbamate;

9-Deoxo-9-amino-11-deoxy-5-O-desosaminyl-11-(3-furan-2-yl-propyl)hydrazo-6-O-methyl-3-oxoerythronolide A, 11,12-carbamate;

9-Deoxo-9-amino-11-deoxy-5-O-desosaminyl-11-(3-thiophen-2-yl-propyl)hydrazo-6-O-methyl-3-oxoerythronolide A, 11,12-carbamate;

9-Deoxo-9-amino-11-deoxy-5-O-desosaminyl-11-(3-pyrrol-1-yl-propyl)hydrazo-6-O-methyl-3-oxoerythronolide A, 11,12-carbamate;

9-Deoxo-9-amino-11-deoxy-5-O-desosaminyl-11-(3-(2-pyridin-3-yl-thiazol-4-yl)-propyl)hydrazo-6-O-methyl-3-oxoerythronolide A, 11,12-carbamate;

9-Deoxo-9-amino-11-deoxy-5-O-desosaminyl-11-(3-(2-phenyl-thiazol-5-yl)-propyl)hydrazo-6-O-methyl-3-oxoerythronolide A, 11,12-carbamate;

9-Deoxo-9-amino-11-deoxy-5-O-desosaminyl-11-(3-(4-phenyl-1H-imidazol-2-yl)-propyl)hydrazo-6-O-methyl-3-oxoerythronolide A, 11,12-carbamate;

and the pharmaceutically acceptable salts of the foregoing compounds.

11. A pharmaceutical composition for the treatment of a bacterial or protozoa an infection in a mammal, fish or bird which comprises a therapeutically effective amount of a compound of claim 1 and a pharmaceutically acceptable carrier.

12. A method of treating a bacterial or protozoa an infection in a mammal, fish, or bird which comprises administering to said mammal, fish, or bird a therapeutically effective amount of a compound of claim 1.

13. A method of preparing a compound of the formula I

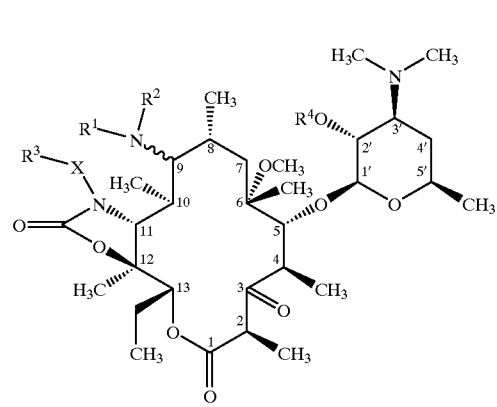

wherein:

X is —CR$^5$R$^6$— or —NR$^5$— or —O—;

or X is taken together with R$^3$ to form —N═CR$^7$R$^8$;

or X and R$^3$ are taken together to form a heterocyclic ring of the formula XI

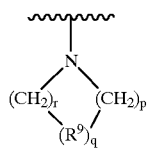

XI wherein in said ring of formula XI, r and p are each independently an integer ranging from 1 to 3, q is 0 or 1, and R$^9$ is —CH$_2$—, —O—, —S—, —C(O)—, —C(S)—, —SO$_2$—, —CH═CH—, —CH(OH)CH(OH)—, or —NH—; and wherein the (CH$_2$)$_r$ and (CH$_2$)$_p$ portions of said ring of formula XI are optionally substituted by 1 to 4 substituents, and the nitrogen atom where R$^9$ is —NH— is optionally substituted by 1 substituent, and each hydrogen atom of R$^9$ where R$^9$ is —CH$_2$—, —CH═CH—, or —CH(OH)CH(OH) is optionally substituted by one substituent, said optional substituents being independently selected from the group consisting of —C(O)O(C$_1$-C$_{10}$ alkyl), C$_1$-C$_{10}$ alkoxy, C$_1$-C$_{10}$ alkanoyl, halo, nitro, cyano, 4–10 membered heterocyclic, C$_1$-C$_{10}$ alkyl, —NR$^5$R$^6$, C$_6$-C$_{10}$ aryl, —S(O)$_n$(C$_1$-C$_{10}$ alkyl) wherein n is an integer ranging from 0 to 2, and —SO$_2$NR$^5$R$^6$;

each R$^1$ and R$^2$ is independently selected from H and C$_1$-C$_2$ alkyl, wherein one or two carbons of said alkyl are optionally replaced by a heteroatom selected from O, S and N, and are optionally substituted by 1 to 3 substituents selected from the group consisting of —C(O)O(C$_1$-C$_{10}$)alkyl, —O(C$_1$-C$_{10}$)alkyl, C$_1$-C$_{10}$ alkanoyl, halo, nitro, cyano, C$_1$-C$_{10}$ alkyl, 4–10 membered heterocyclic, C$_6$-C$_{10}$ aryl, —N(C$_1$-C$_{10}$)alkyl, —S(C$_1$-C$_{10}$ alkyl), —SO(C$_1$-C$_{10}$)alkyl, —SO$_2$(C$_1$-C$_{10}$)alkyl and —SO$_2$N(C$_1$-C$_{10}$)alkyl;

or R$^1$ and R$^2$ are taken together with the nitrogen atom to which they are linked to form —N═CR$^7$R$^8$;

or R$^1$ and R$^2$ are taken together with the nitrogen atom to which they are linked to form a heterocyclic ring of the formula XI

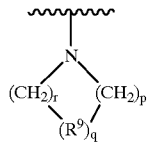

XI wherein in said ring of formula XI, r and p are each independently an integer ranging from 1 to 3, q is 0 or 1, and R$^9$ is —CH$_2$—, —O—, —S—, —C(O)—, —C(S)—, —SO$_2$—, —CH═CH—, —CH(OH)CH(OH)—, or —NH—; and wherein the (CH$_2$)$_r$ and (CH$_2$)$_p$ portions of said ring of formula XI are optionally substituted by 1 to 4 substituents, and the nitrogen atom where R$^9$ is —NH— is optionally substituted by 1 substituent, and each hydrogen atom of R$^9$ where R$^9$ is —CH$_2$—, —CH═CH—, or —CH(OH)CH(OH) is optionally substituted by one substituent, said optional substituents being independently selected from the group consisting of —C(O)O(C$_1$-C$_{10}$ alkyl), C$_1$-C$_{10}$ alkoxy, C$_1$-C$_{10}$ alkanoyl, halo, nitro, cyano, 4–10 membered heterocyclic, C$_1$-C$_{10}$ alkyl, —NR$^5$R$^6$, C$_6$-C$_{10}$ aryl, —S(O)$_n$(C$_1$-C$_{10}$ alkyl) wherein n is an integer ranging from 0 to 2, and —SO$_2$NR$^5$R$^6$;

R$^3$ is H, R$^7$, —C(O)R$^7$, C(O)R$^{10}$, —C(O)OR$^7$, —C(O)OR$^{10}$, or —(CR$^5$R$^6$)$_m$R$^{10}$, wherein m is an integer ranging from 0 to 6 and both R$^5$ and R$^6$ may vary for each interation where m is greater than 1;

R$^4$ is H, —C(O)R$^{10}$ or C$_1$-C$_{18}$ alkanoyl, wherein in the alkyl portion of said alkanoyl one or two carbons optionally may be replaced by a heteroatom selected from O, S and N;

each R$^5$ and R$^6$ is independently H or C$_1$-C$_6$ alkyl;

each R$^7$ and R$^8$ is independently selected from H and C$_1$-C$_{12}$ alkyl, wherein one or two carbons of said alkyl are optionally replaced by a heteroatom selected from O, S and N, and are optionally substituted by 1 to 3 substituents selected from the group consisting of —C(O)O(C$_1$-C$_{10}$)alkyl, —O(C$_1$-C$_{10}$)alkyl, C$_1$-C$_{10}$ alkanoyl, halo, nitro, cyano, C$_1$-C$_{10}$ alkyl, 4–10 membered heterocyclic, C$_6$-C$_{10}$ aryl, —N(C$_1$-C$_{10}$)alkyl, —S(C$_1$-C$_{10}$ alkyl), —SO(C$_1$-C$_{10}$)alkyl, —SO$_2$(C$_1$-C$_{10}$)alkyl and —SO$_2$N(C$_1$-C$_{10}$)alkyl; and R$^{10}$ is a 4–10 membered heterocyclic or C$_6$-C$_{10}$ aryl; wherein said heterocyclic and aryl groups are optionally substituted by 1 to 3 substituents independently selected from the group consisting of 4–10 membered heterocyclic, C$_6$-C$_{10}$ aryl, —NHC(O)(C$_1$-C$_{10}$)alkyl, —NHC(O)N(C$_1$-C$_{10}$)alkyl, —C(O)O(C$_1$-C$_{10}$ alkyl, —O(C$_1$-C$_{10}$)alkyl, C$_1$-C$_{10}$)alkanoyl, halo, nitro, cyano, (C$_1$-C$_{10}$) alkyl, —N(C$_1$-C$_{10}$)alkyl, —S(C$_1$-C$_{10}$ alkyl), —SO(C$_1$-C$_{10}$)alkyl), —SO$_2$(C$_1$-C$_{10}$)alkyl and —SO$_2$N(C$_1$-C$_{10}$)alkyl, which comprises treating a compound of the formula II

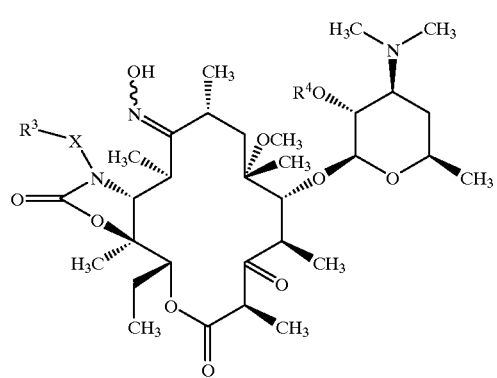

II wherein X, R$^3$, and R$^4$ are as defined above, with a reducing agent.

14. The method of claim 13 wherein the reducing agent is TiCl$_3$.

* * * * *